United States Patent [19]

Trybulski et al.

[11] Patent Number: 5,478,939
[45] Date of Patent: Dec. 26, 1995

[54] (R,R) AND (S,S) 2,5-DIAZABICYCLO [2,2,1]HEPTANE DERIVATIVES

[75] Inventors: Eugene Trybulski, Park Ridge; Jing Zhang, E. Brunswick, both of N.J.

[73] Assignee: American Cyanamid Company, Wayne, N.J.

[21] Appl. No.: 277,886

[22] Filed: Jul. 20, 1994

[51] Int. Cl.$^6$ ............... C07D 487/04; A61K 31/495; A61K 31/425; A61K 31/41

[52] U.S. Cl. ........... 544/336; 544/408; 544/409; 548/128; 548/133; 548/181; 548/453; 514/254; 514/361; 514/364; 514/370; 514/412; 514/414

[58] Field of Search ............... 544/349, 336, 544/408, 409; 548/128, 133, 181, 453; 514/254, 361, 370, 412, 414, 364

[56] References Cited

U.S. PATENT DOCUMENTS

| | | | |
|---|---|---|---|
| 4,994,460 | 2/1991 | Dextraze et al. | 514/252 |
| 5,036,163 | 7/1991 | Braish et al. | 548/542 |
| 5,073,557 | 12/1991 | Baker et al. | 514/254 |
| 5,405,853 | 4/1995 | Baker et al. | 514/299 |

OTHER PUBLICATIONS

Gray et al, *Trends in Pharmacological Sciences*, pp. 85–88 (Dec. 1989).
Quirion et al, *Trends in Pharmacological Sciences* (Dec., 1989, supplement), pp. 80–84.
Portoghese et al, J. Org. Chem., 1966, 31:1059.
Portoghese et al., Tetrahedron, 1971, 27:1823–1829.
Carroll, F. I. et al., J. Med. Chem., 1992, 35:2184–2191.
Carroll, P. J. et al., J. Med. Chem., 1992, 35:305–309.
Showell, G. A. et al., J. Med. Chem., 1992, 35:911–916.
Street, L. J. et al., J. Med. Chem., 1990, 33:2690–2697.
Wadsworth, H. J., et al., J. Med. Chem., 1992, 35:1280–1290.
Jenkins, S. M., et al., J. Med. Chem., 1992, 35:2392–2406.
Macleod, A. M., et al., J. Med. Chem., 1990, 33:2052–2059.

*Primary Examiner*—Emily Bernhardt
*Attorney, Agent, or Firm*—Richard K. Jackson

[57] ABSTRACT

Compounds of the Formulae I or II

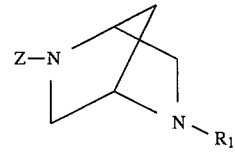

I

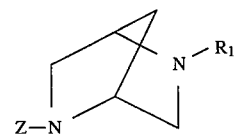

II wherein Z and $R_1$, are as described herein which compounds are muscarinic agonists useful in treating central cholinergic disfunction and pharmaceutical compositions containing the compounds.

33 Claims, No Drawings

(R,R) AND (S,S) 2,5-DIAZABICYCLO [2,2,1] HEPTANE DERIVATIVES

BACKGROUND OF THE INVENTION

The design of novel CNS-active muscarinic agonists requires the incorporation of two pharmacophoric groups into the molecule:

a) a basic sp3-nitrogen atom which at pH 7.4 is protonated and mimics the quarternary nitrogen atom in acetylcholine; and b) an ester functionality, or bioequivalent, to substitute for the acetyl group of the neurotransmitter.

The discovery of a series of five and six membered heteroaromatic rings that can be substituted for the ester functionality has led to numerous muscarinic agents which do not suffer from the hydrolyric instability that has been a serious drawback to acetylcholine mimics (such as arecoline and aceclidine). The attachment or connection of the two pharmacophoric groups has been accomplished using carbon-carbon bonds usually incorporated into a ring. The 1-azabicyclo[2.2.2] octane and 1-azabicyclo[2.2.1]heptane derivatives are examples of this strategy. (Showell, G. A. et al, *J. Med. Chem.*, 1992, 35, 911–916; Street, L. J. et al, *J. Med. Chem.*, 1990, 33, 2690–2697; MacLeod, A. M. et al, *J. Med. Chem.*, 1990, 33, 2052–2059).

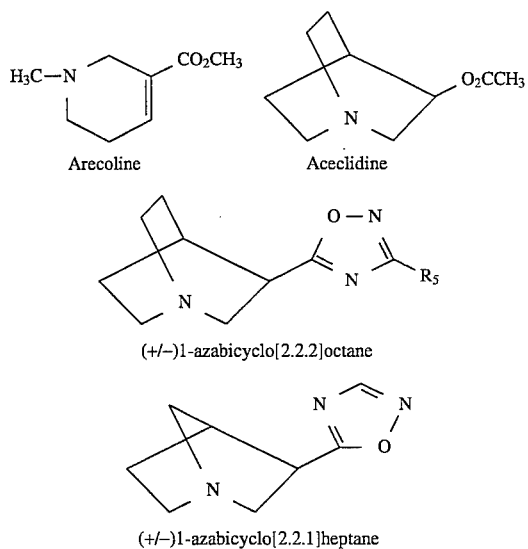

The optimal level of potency and efficacy for the prototype muscarinic agent for the treatment of cognitive disorders has not been determined. A series of compounds with a broad range of activity is needed to determine which if any possess a useful level of cholinergic activity. The relative position of the two pharmacophoric groups within the molecule helps to determine the potency and the efficacy of the molecules as muscarinic agents. In relation to the 1-azabicyclo derivatives, F. I. Carrol, *J. Med. Chem.*, 1992, 35, 2184, demonstrated that by increasing the distance between the pharmacophoric groups by moving the basic nitrogen atom further from the ester functionality (1-aza- to 2-azabicyclo[2.2.1]heptane derivative), the muscarinic agonist activity is retained but with less potency. A drawback of these 2-aza- derivatives is the hydrolyric stability of the ester functionality.

SUMMARY OF THE INVENTION

The invention is concerned with compounds of Formulae I and II:

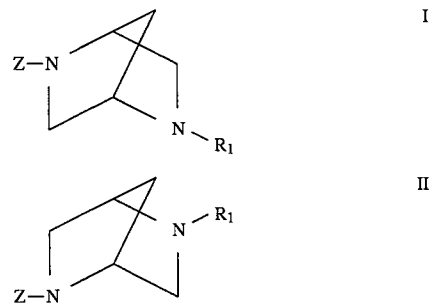

wherein
Z is hydrogen, methyl, $(C_1-C_{10})$alkyloxycarbonyl or arylmethyloxycarbonyl such as benzyloxycarbonyl; $R_1$ is

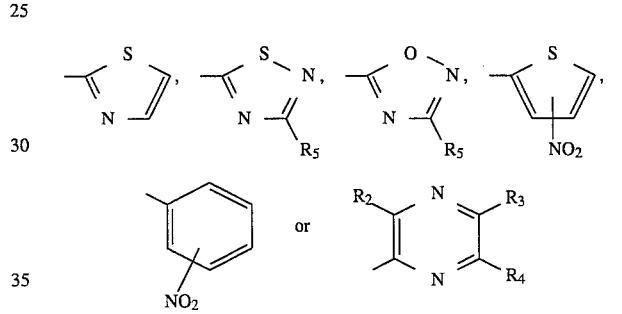

wherein
$R_2$, $R_3$ and $R_4$ are hydrogen; halogen selected from bromine, chlorine, fluorine and iodine; $(C_1-C_6)$alkyl or $(C_1-C_6)$alkyloxy; and $R_5$ is hydrogen or $(C_1-C_6)$alkyl; and the pharmacologically acceptable salts thereof.

DESCRIPTION OF THE PREFERRED EMBODIMENT

The novel compounds, represented by Formulae I and II, of the present invention:

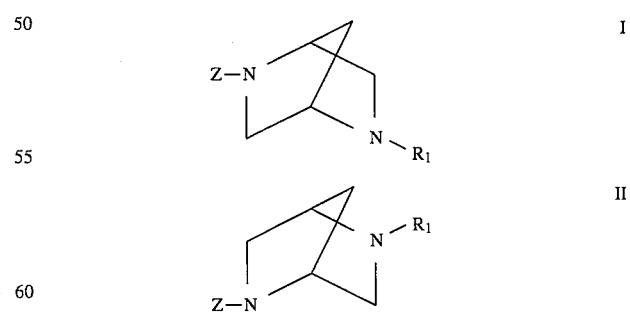

may be prepared in accordance with one of the following schemes.

Scheme 1

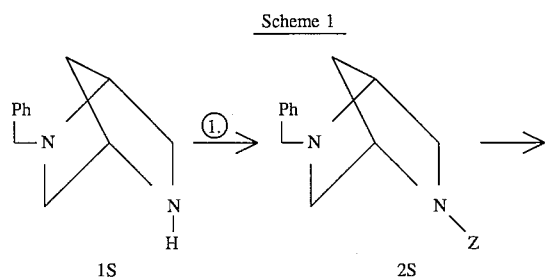

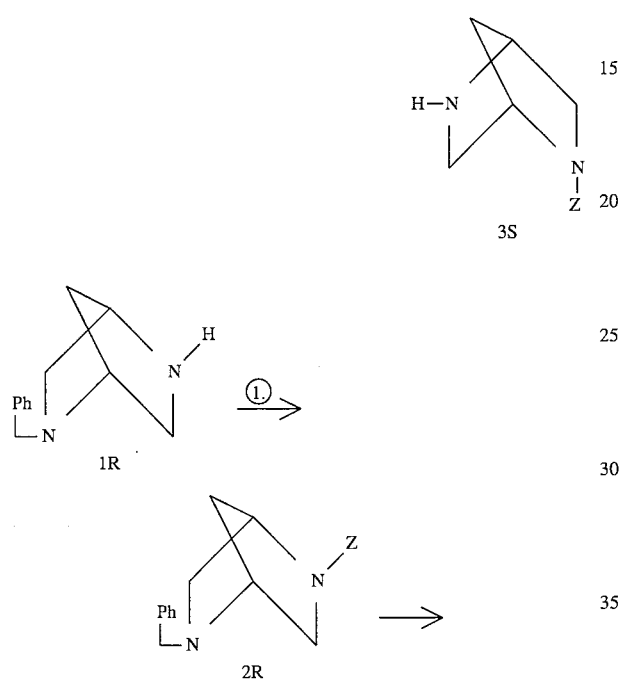

① Z—Cl, Z = (C₁–C₁₀)alkyl-O—C—
                              ‖
                              O In Scheme 1, compound 1S or 1R, prepared by the procedure of P. S. Portoghese, *J. Org. Chem.*, 1966, 31, 1059 or U. Jordis, *Synthesis*, 1990, 925, is reacted with an (C₁-C₁₀)alkyl chloroformate, Z-Cl, in the presence of a tertiary amine such as triethylamine or diazabicycloundecene in an inert solvent such as diethyl ether or methylene chloride at or near room temperature to provide a compound of general formula 2S or 2R. Compound 2S or 2R is reacted with hydrogen at between atmospheric pressure and 50 psi in the presence of a catalyst such as platinum oxide or palladium on carbon in an alcohol solvent such as ethyl alcohol at or near room temperature to afford a compound of general formula 3S or 3R wherein Z is (C₁-C₁₀)alkyloxycarbonyl.

Scheme 2

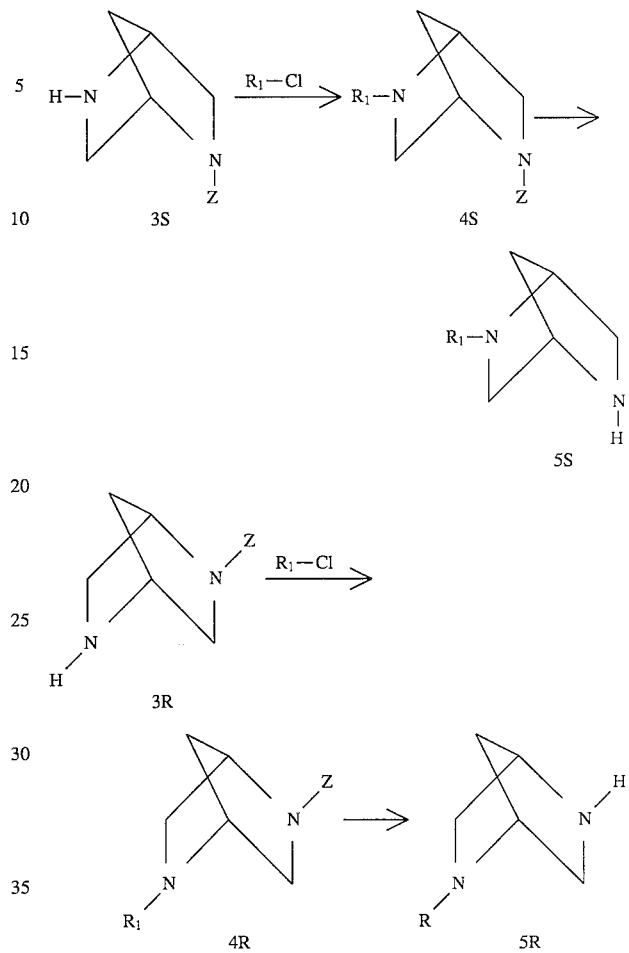

In accordance with Scheme 2, 3S or 3R is reacted with a halo-substituted heteroaromatic, R₁Cl wherein R₁ is as hereinbefore described such as 2-chloropyrazine, 2-chlorothiazole, 5-chloro-3-methyl-1,2,4-thiadiazole, a 2- or 4-halo substituted nitrobenzene or a 2-halo-3- or 5-nitro substituted thiophene, in an inert solvent such as diethyl ether or methylene chloride, at or between room temperature and the reflux temperature of the solvent to afford the compound 4S or 4R. The compound of formula 4S or 4R, wherein Z is (C₁-C₁₀)alkyloxycarbonyl or arylmethyloxycarbonyl, is reacted with a strong acid such as trifluoroacetic acid or hydrochloric acid, in an inert solvent such as diethyl ether, methylene chloride or ethyl alcohol, at or between room temperature and the reflux temperature of the solvent, to give the product 5S or 5R.

Scheme 3

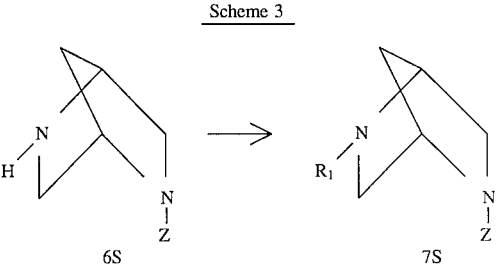

-continued
Scheme 3

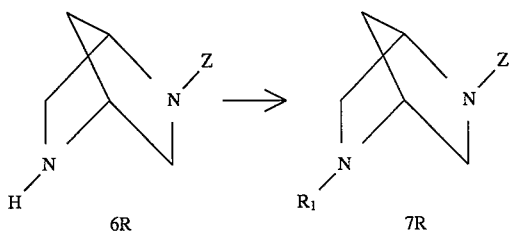

As illustrated in Scheme 3, 6S or 6R, prepared by the procedure of U. Jordis, *Synthesis,* 1990, 925, wherein Z is $(C_1-C_6)$alkyl, is reacted with a halo-substituted heteroaromatic, $R_1Cl$ wherein $R_1$ is as hereinbefore described such as 2-chloropyrazine, 2-chlorothiazole, 5-chloro-3-methyl-1,2,4-thiadiazole, a 2- or 4-halo substituted nitrobenzene or a 2-halo-3- or 5-nitro substituted thiophene, in an inert solvent such as diethyl ether or methylene chloride, at or between room temperature and the reflux temperature of the solvent to afford the compound of formula 7S or 7R.

Scheme 4

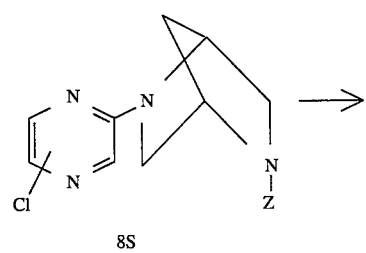

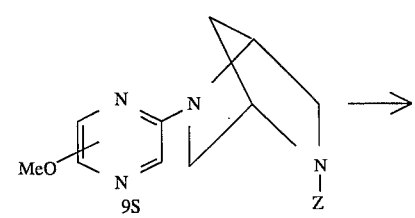

-continued
Scheme 4

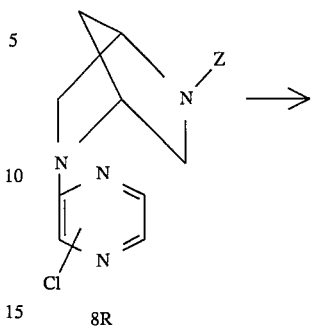

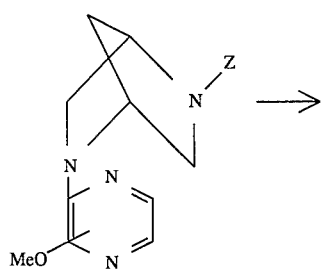

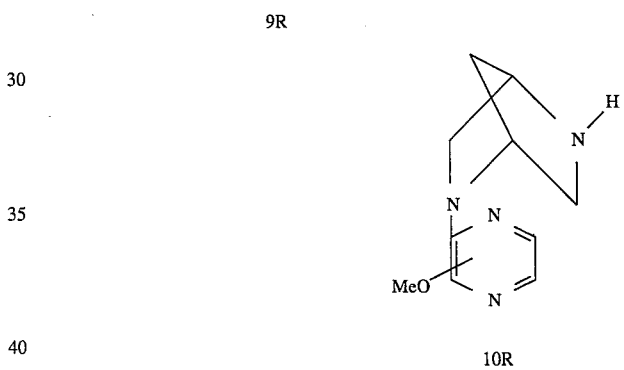

In accordance with Scheme 4 wherein Z is hydrogen, methyl, $(C_1-C_{10})$alkyloxycarbonyl or arylmethyloxycarbonyl; a compound of formula 8S or 8R is reacted with an alkali metal lower alkoxide in the corresponding alcohol solvent or other polar aprotic solvent such a dimethylformamide, at or between room temperature and the reflux temperature of the solvent, to give the product 9S or 9R. A compound of formula 9S or 9R wherein Z is $(C_1-C_{10})$alkyloxycarbonyl or arylmethyloxycarbonyl, is reacted with a strong acid such as trifluoroacetic acid or hydrochloric acid in an inert solvent such as diethyl ether, methylene chloride, or ethyl alcohol at or between room temperature and the reflux temperature of the solvent to give the product of formula 10S or 10R.

Scheme 5

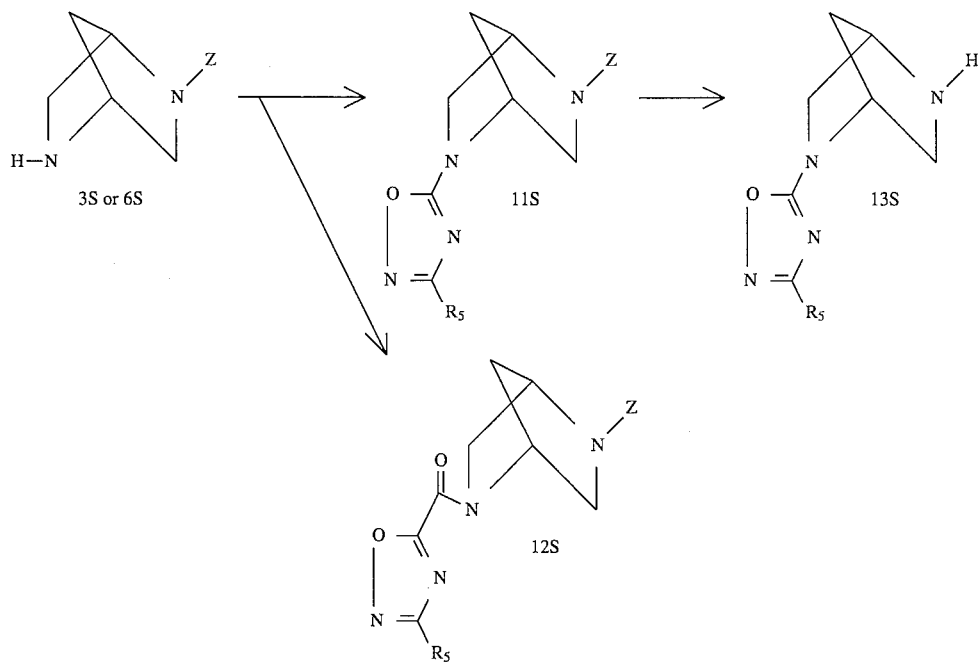

In accordance with Scheme 5, a compound of formula 3S, wherein Z is ($C_1$–$C_{10}$) alkyloxycarbonyl or arylmethyloxycarbonyl, or 6S, wherein Z is ($C_1$–$C_6$)alkyl, is reacted with 3-methyl-5-trifluoro-methyl-1,2,4-oxadiazole, prepared by the procedure of Eloy, *Helv. Chim. Acta,* 1966, 40, 1430, either neat or in an inert non-polar solvent such as toluene at or near room temperature to give a separable mixture of 11S, the desired product, and 12S a reaction by-product. Compound 11S (or the other enantiomer 11R), wherein Z is ($C_1$–$C_{10}$)alkyloxycarbonyl or arylmethyloxycarbonyl, is reacted with a strong acid such as trifluoroacetic acid or hydrochloric acid in an inert solvent such as diethyl ether, methylene chloride or ethyl alcohol, at or between room temperature and the reflux temperature of the solvent to give the product of formula 13S (or 13R).

The compounds described in this invention contain an additional nitrogen atom, an isostere, in the bicyclo [2.2.1] ring system at the point of attachment of a hydrolyrically stable acetate bioequivalent. The substitution of the C-5 carbon for a sp3-nitrogen atom provides additional electron density to the heterocyclic ring attached at the 5-position without a substantial change to the structure of the target molecule.

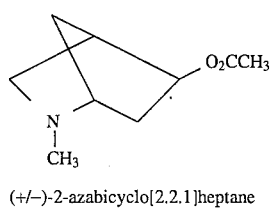

(+/−)-2-azabicyclo[2.2.1]heptane

-continued

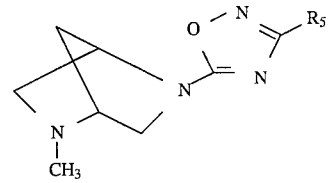

(R,R)-2,5-diazabicyclo[2.2.1]heptane

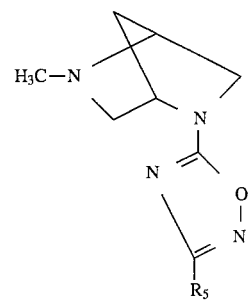

(S,S)-2,5-diazabicyclo[2.2.1]heptane

The addition of the nitrogen atom could be considered detrimental to the cholinergic activity of the molecules since an additional group which can be protonated is introduced. To avoid protonation of the newly introduced nitrogen atom at physiological pH, amino substituted heteraromatic groups were selected that had a $pK_b > 7.4$.

The modifications that result improve the hydrolyric stability (the heterocyclic ring as a bioequivalent of the acetate in acetyl choline), increase the electron density of the heterocyclic ring (the substitution of the nitrogen atom as compared to the carbon substituted heterocycle) and provide a series of secondary amino derivatives that are amenable to pro-drug formulation.

Biological Protocols

[³H] Quinuclidinyl Benzilate Binding Assay:

This assay is utilized in conjunction with the ³H-cis-methyldioxolane binding assay to evaluate antagonist and high affinity agonist binding properties of CNS cholinergic agents. The procedure was adopted from Watson, M., Yamamura, H. I., and Roeske, W. R., *J. Pharmacol. Exp. Ther.*, 237:411–418 (1986) and Watson, M., Roeske, W. R., and Yamamura, H. I., *J. Pharmacol. Exp. Ther.*, 237:419–427 (1986).

Tissue Preparation:

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds:

A stock solution of Atropine is prepared at 0.2 mM to define non-specific binding (1 μM final conc). Test compound are prepared at 40 mM (final conc 1 mM) in buffer (if water soluble) or in absolute ethanol—1N HCl (1:1, v/v) and serially diluted to the desired concentrations. In general, dose-response profiles are examined between 1 mM and 1 pM final concentrations.

Preparation of ³H-QNB:

³H-QNB (NEN, NET-656; specific activity= 30.0 Ci/mmol) is diluted to 5 nM, with NaPB (final concentration=0.25 nM activity 18,000 cpm at a counting efficiency of 55%).

³H-QNB Binding Assay:

A typical protocol is outlined below:

| Tube No. | ID* | Buffer μl | Atropine μl | Test Compound μl | ³H-QNB μl | Tissue ml |
|---|---|---|---|---|---|---|
| 1-2 | Total | 50 | — | — | 100 | 1.85 |
| 3-4 | NS | 40 | 10 | — | " | " |
| 4-6 | 4e-11 | — | — | 50 | " | " |
| 5-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of the 120 minutes, the samples are filtered through GF/B glass fiber filters (Whatman) using a 24 sample cell harvester (Brandel) under a vacuum of 15 mmHg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total—NS (non-specific). The percent inhibition of specific binding is then calculated and the Ki values computed using either the LIGAND or LUNDON software packages for competition binding. The results of this test on representative compounds of this invention appear in Table I.

[³H]-cis-Methyldioxolane Binding Assay (High Affinity):

This assay is utilized in conjunction with ³H-QNB binding to evaluate high affinity agonist binding and antagonist properties of CNS cholinergic agents. The procedure was adapted from Vickroy, T. W., Roeske, W. R., and Yamamura, H. I., *J. Pharmacol. Exp. Ther.*, 229:747–755 (1984). This is a rapid filtration assay that is set up to label only the high affinity agonist conformation of the muscarinic cholinergic receptor.

Tissue Preparation:

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds:

A stock solution of Atropine is prepared at 0.2 mM to define non-specific binding (1 μM final conc). Test compound are prepared at 40 mM (final conc 1 mM) in buffer (if water soluble) or in absolute ethanol—1N HCl (1:1, v/v) and serially diluted to the desired concentrations. In general, dose-response profiles are examined between 1 mM and 1 pM final concentrations.

Preparation of ³H-CD:

³H-CD (NEN, NET-647; specific activity= 55.5 Ci/mmol) is diluted to 20 nM with NaPB (final conc= 1.0 nM, activity 75,000 cpm at a counting efficiency of 55%).

Technical Notes:

³H-CD adheres readily to both glass and plastic surfaces. To eliminate this problem (and the chance for introducing artifacts into the results), stock vials, pipette tips and all glass tubes are routinely treated with Prosil-28, a siliconizing agent, and oven dried prior to use in an assay. Additionally, the GF/B glass fiber filters are presoaked in an aqueous polyethylenimine (PEI) solution (0.1%, pH 7.0) prior to use.

All points in the inhibition curve (including total and non-specific binding) are always measured on single PEI treated filter strips to minimize filter-to-filter variability. (See Bruns, R. F. et al, *Ana. Biochem.*, 132:74–81 (1983) for the use of PEI treated filters in filtration receptor assays).

The ³H-CD is prepared fresh in buffer just prior to use in the assay to avoid possible decomposition. It should be kept in an ice bath after dilution in buffer.

³H-CD Binding Assay:

A typical protocol is outlined below:

| Tube No. | ID* | Buffer μl | Atropine μl | Test Compound μl | ³H-QNB μl | Tissue ml |
|---|---|---|---|---|---|---|
| 1-2 | Total | 50 | — | — | 100 | 1.85 |
| 3-4 | NS | 40 | 10 | — | " | " |
| 4-6 | 4e-11 | — | — | 50 | " | " |
| 5-8 | 4e-10 | — | — | " | " | " |

-continued

| Tube No. | ID* | Buffer μl | Atropine μl | Test Compound μl | ³H-QNB μl | Tissue ml |
|---|---|---|---|---|---|---|
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | ". | " | " |
| 23-24 | 4e-02 | — | — | " | " | " |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of the 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total—NS (non-specific). The percent inhibition of specific binding is then calculated and the Ki values computed using either the LIGAND or LUNDON software packages for competition binding. The results of this test on representative compounds of this invention appear in Table I.

TABLE I

| Example No. | Ki, μM ³H-QNB (ctx) | Ki, μM ³H-CD (ctx) | Ratio ³H-QNB (ctx) ³H-CD (ctx) |
|---|---|---|---|
| 9 | ND | 18.2 | |
| 10 | ND | 43.2 | |
| 3 | >1000 | >1000 | >100 |
| 7 | | >1000 | ND |
| 8 | ND | 97 | |
| 5 | >1000 | 59 | |
| 6 | ND | ND | |
| 18 | 47.2 | 0.4 | 108.2 |
| 17 | >1000 | 5.4 | |
| 11 | 3.1 | 0.1 | 53.7 |
| 12 | 11.4 | 1.3 | 8.8 |
| 16 | >1000 | 0.3 | |
| 15 | >1000 | 29.5 | |
| 14 | 24.7 | 0.9 | 29 |
| 13 | Nd | 13 | |
| 30 | 1.6 | 1.1 | 1.5 |
| 32 | 0.4 | 0.3 | 1.3 |
| 33 | >1000 | 7.5 | |
| 37 | 2 | 0.1 | 17.8 |
| 19 | 5.5 | 0.4 | 13.8 |
| 22 | 1.2 | 0.7 | 1.9 |
| 23 | 2.3 | 0.9 | 2.6 |
| 35 | 6.3 | 1.7 | 3.7 |
| 38 | 9.8 | 2.9 | 3.4 |
| 24 | 4.5 | 2 | 2.3 |
| 36 | >1000 | 6.4 | |
| 26 | 0.5 | 0.2 | 2.7 |
| 28 | >1000 | 9.8 | |
| 29 | 13.2 | 6.8 | 1.9 |

Those compounds which have ³H-CD and optimally ³H-QNB Ki values of less than 100 μM are considered active. The compounds tested can be divided into 3 categories:

1. compounds which are products or therapeutic agents;
2. compounds which are a pro-drug form of the products or therapeutic agents and
3. compounds which are reaction intermediates.

The pharmaceutical preparations of the present invention may contain, for example, from about 0.5% up to about 90% of the active ingredient in combination with the carrier, more usually between 5% and 60% by weight.

The effective dosage of active ingredient employed may vary with the particular compound employed, the mode of administration, and the severity of the condition being treated. In general, however, satisfactory results are obtained when the compound of the invention are administered at a daily dosage of from about 0.02 mg to about 100 mg/kg of patient body weight, preferably given in divided doses two to four times a day, or in sustained release form. For most patients, the total daily dosage is from about 1 mg to 5,000 mg, preferably from about 1 mg to 20 mg. Dosage forms suitable for internal use comprise from about 0.25 to 5.0 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by exigencies of the therapeutic situation.

A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, nonionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, and antioxidants, e.g. vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compound is preferred.

These active compounds may also be administered parenterally or intraperitoneally. Solutions or suspensions of the active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

As used herein, "pharmaceutically acceptable carrier" includes any and all solvents, dispersion media, coating, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated.

The following examples describe in detail the chemical synthesis of representative compounds of the present invention. The procedures are illustrations, and the invention should not be construed as being limited by chemical reactions and conditions they express. No attempt has been made to optimize the yield obtained in these reactions, and it would be obvious to one skilled in the art that variations in reaction times, temperatures, solvents, and/or reagents could increase the yields.

EXAMPLE 1

(R,R)-2-(tert-Butyloxycarbonyl)-2,5-diazabicyclo[2.2.1] heptane

A mixture of 3.6 g of (R,R) -5-benzyl-2-(tertbutyloxycarbonyl)- 2,2-diazabicyclo[2.2.1] heptane, prepared by the procedure of Jordis et al, *Synthesis*, 1990, 925, and 2.2 g of 10% palladium on carbon in 140 ml of methyl alcohol is hydrogenated in a Parr apparatus at 40 pounds per square inch (psi) for 16 hours. The reaction is filtered through a pad of diatomaceous earth and the filtrate is concentrated in vacuo. The residue is purified by column chromatography (aluminum oxide, 2.5 activity grade; 2% methyl alcohol/ methylene chloride) to give 1.14 g of the desired product as pale yellow crystals:

mp 62°–63° C.

EXAMPLE 2

(S,S)-2-(tert-Butyloxycarbonyl)-2,5-diazabicyclo [2.2.2]heptane

A mixture of 4.8 g of (R,R)-5-benzyl-2-(tertbutyloxycarbonyl)- 2,5-diazabicyclo[2.2.1] heptane, prepared by the procedure of Jordis et at, and 1.77 g of 10% palladium on carbon in 60 ml of methyl alcohol is hydrogenated in a Parr apparatus at 40 psi for 16 hours. The reaction is filtered through a pad of diatomaceous earth and the filtrate is concentrated in vacuo. The residue is purified by column chromatography (aluminum oxide, 2.5 activity grade; 2% methyl alcohol/methylene chloride) to give 2.87 g of the desired product as yellow crystals:

mp 62°–63° C.

EXAMPLE 3

(R,R)-2-(tert-Butyloxycarbonyl)-5-(2-pyrazinyl)- 2,5-diazabicyclo[2.2.1] heptane A solution of 4.0 g of product from Example 1, 5.0 g of 2-chloropyrazine and 4.4 g of diazabicyclo[ 3.6.0]undecene-5 in 15 ml of triethylamine is heated at reflux temperature over night. The reaction mixture is cooled, diluted with toluene and concentrated in vacuo to dryness. The residue is diluted with methylene chloride and washed with 5N sodium hydroxide. The organic layer is dried over anhydrous sodium sulfate, passed through a pad of hydrous magnesium silicate, and concentrated in vacuo to give 8.8 g of a dark brown oil. Purification of the oil (silica gel; 40% hexane/ethyl acetate) gives 4.2 g of the desired product as off white crystals:

mp= 127°–128° C.;

$[\alpha]_{26°}^{D}=+246°$ (c=1.0%), methyl alcohol.

EXAMPLE 4

(S,S)-2-(tert-Butyloxycarbonyl)-5-(2-pyrazinyl)- 2,5-diazabicyclo[2.2.1] heptane The title compound is prepared by the procedure of Example 3 using the product from Example 2 and 2-chloropyrazine to give 1.6 g of the desired product:

mp 125°–126° C.;

$[\alpha]_{26°}^{D}=-241°$ (c=1.0%), methyl alcohol.

EXAMPLE 5

(R,R)-2-tert-Butyloxycarbonyl)-5-(3-methyl- 1,2,4-thiadiazol- 5-yl)-2,5-diazabicyclo[2.2.1]heptane A solution of 1.4 g of 5-chloro-3-methyl-1,2,4-thiadiazole, prepared by the procedure of J. Goerdeler, *Chin. Ber.*, 1957, 90, 182, in 4 ml of tetrahydrofuran is added over one hour to a solution of 0.9 g of product from Example 1 and 0.72 g of potassium carbonate in 20 ml of tetrahydrofuran. The reaction mixture is stirred at room temperature overnight. The reaction is diluted with methylene chloride, washed with water and the layers are separated. The organic layer is dried over anhydrous sodium sulfate and concentrated in vacuo to dryness. The residue is purified by chromatography (aluminum oxide, Activity Grade 2.5; 2% methyl alcohol/methylene chloride) to give 0.94 g of the desired product as a pale yellow oil:

$[\alpha]_{26°}^{D}=+186°$ (c=0.6%), methyl alcohol.

EXAMPLE 6

(S,S)-2-(tert-Butyloxycarbonyl)-5-(3-methyl- 1,2,4-thiadiazol- 5-yl)-2,5-diazabicyclo[2,2,1]heptane The title compound is prepared by the procedure of Example 5 using 5-chloro-3-methyl-1,2,4-thiadiazole prepared as above, the product from Example 2 and potassium carbonate to give 2.48 g of the desire product:

$[\alpha_{26°}^{D}=-209°$ (c=1.2%), methyl alcohol.

EXAMPLE 7

(R,R,)-2-(tert-Butyloxycarbonyl-5-(1,2,4- thiadiazol-5-yl)- 2,5-diazabicyclo[2.2.1]heptane The title compound is prepared by the procedure of Example 5 using the product from Example 1, 5-chloro-1,2,4-thiadiazole prepared by the procedure of J. Goerdeler, *Chim. Ber.*, 1957, 90, 182, and potassium carbonate to give 0.94 g of the desired product:

$[\alpha_{26°}^{D}=+175°$ (c=1.3%), methyl alcohol.

EXAMPLE 8

(S,S)-2-(tert-Butyloxycarbonyl)-5-(1,2,4-thiadiazol- 5-yl)- 2,5-diazabicyclo[2.2.1] heptane The title compound is prepared by the procedure of Example 5 using the product from Example 2, 5-chloro-1,2,4-thiadiazole prepared as above, and potassium carbonate to give 2.4 g of the desired product:

$[\alpha_{26°}^{D}=-190°$ (c=1.0%), methyl alcohol.

EXAMPLE 9

(R,R)-2-(tert-Butyloxycarbonyl)-5-(3-methyl-1,2,4-oxadiazol-5-yl)-2,5-diazabicyclo[2.2.1] heptane A solution of 1.06 g of 3-methyl-5-trichloromethyl-1,2,4-oxadiazole prepared by the procedure of F. Eloy, *Bull. Soc. Chim. Belg.*, 1964, 73, 793, in 2 ml of toluene is added slowly to a solution of 1.05 g of product from Example 1 and 0.82 g of diazabicyclo[3.6.0]unodecene-5 in 1 ml of toluene. The resulting mixture is stirred at room temperature for 3 days and then concentrated in vacuo to dryness. The residue is purified by chromatography (aluminum oxide, Activity Grade 2.5; methylene chloride) to give 0.74 g of the desired product as an off-white solid:

mp= 103°–104° C.;

$[\alpha_{26°}^D=+188°$ (c=0.8%), methyl alcohol.

EXAMPLE 10

(S,S)-2-(tert-Butyloxycarbonyl)-5-(3-methyl-1,2,3-oxadiazol-5-yl)-2,5-diazabicyclo[2.2.1] heptane The title compound is prepared by the procedure of Example 9 using the product from Example 2 and 3-methyl-5-trichloromethyl-1,2,4-oxadiazole prepared as above, to give 0.21 g of the desired product:

mp= 104°–105° C.;

$[\alpha_{26°}^D=-167°$ (c=1.0%), methyl alcohol.

EXAMPLE 11

(R,R)-2-(2-Pyrazinyl)-2,5-diazabicyclo[2.2.1]heptane hydrochloride

A solution of 3.2 g of product from Example 3 and 58 ml of 1N methanolic hydrogen chloride is stirred at room temperature overnight. The reaction is concentrated in vacuo to dryness, diluted with isopropyl alcohol and reconcentrated in vacuo to dryness. The residue is recrystallized from a mixture of isopropanol/diethyl ether to give 2.1 g of the desired product as pale yellow crystals:

mp= 255° C. (dec);

$[\alpha_{26°}^D=+34°$ (c=0.5%), methyl alcohol.

EXAMPLE 12

(S,S)-2-(2-Pyrazinyl)-2,5-diazabicyclo[2.2.1]heptane hydrochloride

The title compound is prepared by the procedure of Example 11 using the product from Example 4 and 1N methanolic hydrogen chloride to give 0.4 g of the desired product:

mp= 255° C. (dec);

$[\alpha_{26°}^D=-34°$ (c=1.0%), methyl alcohol.

EXAMPLE 13

(S,S)-2-(3-Methyl-1,2,4-thiadiazol-5-yl)-2,5-diazabicyclo[2.2.1] heptane

A solution of 1.07 g of product from Example 6 and 2.0 ml of trifluoroacetic acid in 20 ml of methylene chloride is stirred at room temperature overnight. The trifluoroacetic acid reaction mixture is treated with 1N sodium hydroxide until the solution is basic. The mixture is concentrated in vacuo to dryness and the residue is purified by chromatography (aluminum oxide, Activity Grade 2.5; 1–5% methyl alcohol/methylene chloride gradient); followed by short path distillation (0.005 mm Hg, 60°–100° C.) to give 0.67 g of the desired product as a colorless oil:

$[\alpha_{26°}^D=-150°$ (c=0.9%), chloroform;

MS(FAB): m/z 196 M+.

EXAMPLE 14

(R,R)-2-(3-Methyl-1,2,4-thiadiazol-5-yl)-2,5-diazabicyclo[2.2.1] heptane

The title compound is prepared by the procedure of Example 13 using the product from Example 5 and trifluoroacetic acid.

MS(FAB): m/z 196 M$^+$.

EXAMPLE 15

(S,S)-2-(1,2,4-Thiadiazol-5-yl)-2,5-diazabicyclo[2.2.1]heptane

The title compound is prepared by the procedure of Example 13 using the product of Example 8 and trifluoroacetic acid.

$[\alpha_{26°}^D=-151°$ (c=0.8%), chloroform.

EXAMPLE 16

(R,R)-2-(1,2,4-Thiadiazol-5-yl)-2,5-diazabicyclo[2.2.1]heptane

The title compound is prepared by the procedure of Example 13 using the product of Example 7 and trifluoroacetic acid.

MS(FAB): m/z 182 M$^+$.

EXAMPLE 17

(S,S)-2-(3-Methyl-1,2,4-oxadiazol-5-yl)-2,5-diazabicyclo[2.2.1] heptane

The title compound is prepared by the procedure of Example 13 using the product from Example 10 and trifluoroacetic acid.

$[\alpha_{26°}^D=-98°$ (c=1.0%), chloroform.

EXAMPLE 18

(R,R)-2-(3-Methyl-1,2,4-oxadiazol-5-yl)-2,5- diazabicyclo[2.2.1] heptane

The title compound is prepared by the procedure of Example 13 using the product from Example 9 and trifluoroacetic acid.

MS(FAB): m/z 180 M$^+$.

EXAMPLE 19

(S,S)-2-Methyl-5-(2-pyrazinyl)-2,5-diazabicyclo[2.2.1]heptane

A solution of 2.1 g of (S,S)-2-methyl-2,5-diazabicyclo[2.2.1] heptane prepared by the procedure of U. Jordis et al, *Synthesis*, 1990, 925, and 1.8 ml of 2-chloropyrazine in 8 ml of diazabicyclo[3.6.0]undecene-5 is heated to approximately 80° C. for 2 hours. The reaction solution is cooled, diluted with 100 ml of methylene chloride and washed with 30 ml of 5N aqueous sodium hydroxide. The organic layer is dried and concentrated in vacuo to dryness. The residue is purified by chromatography (aluminum oxide, Activity Grade 2.5; methylene chloride to 5% methyl alcohol/methylene chloride) to give 2.1 g of the desired product as a pale yellow oil:

$[\alpha_{26°}^D]=-126°$ (c=1.07), methyl alcohol.

EXAMPLE 20

(S,S)-2-Methyl-5-(3-methyl-1,2,4-thiadiazol-5-yl)-2,5-diazabicyclo[2.2.1]heptane A solution of 1.04 g of 5-chloro-3-methyl-1,2,4-thiadiazole, prepared by the procedure of J. Goerdeler, *Chim. Ber.*, 1957, 90, 182, in 2 ml of tetrahydrofuran is added over one hour to a solution of 0.825 g of (S,S)-2-methyl- 2,5-diazabicyclo[2.2.1]heptane and 0.77 g of potassium carbonate in 10 ml of tetrahydrofuran. The reaction mixture is stirred at room temperature overnight, diluted with methylene chloride and the organic layer is washed with water. The methylene chloride solution is dried and concentrated in vacuo to dryness. The residue is purified by chromatography (aluminum oxide, Activity Grade 2.5: 2% methyl alcohol/methylene chloride) to give 0.56 g of the desired product:

$[\alpha]_{26°}^D=-241°$ (c=1.0%), methyl alcohol.
MS (FAB) m/z 210 M$^+$.

EXAMPLE 21

(R,R)-2-Methyl-5-(2-pyrizinyl)-2,5-diazabicyclo[2,2,1]heptane

The title compound is prepared by the procedure of Example 19 using (R,R)-2-methyl-2,5-diazabicyclo[ 2.2.1] heptane, prepared by the procedure of Jordis et al, and 2-chloropyrazine.

$[\alpha]_{26°}^D=-200°$ (c=0.2%), methyl alcohol.

EXAMPLE 22

(S,S)-2-(3,6-Dimethylpyrazin-2-yl)-5-methyl-2,5-diazabicyclo[2,2.1] heptane

The title compound is prepared by the procedure of Example 19 using 2-chloro-3,6-dimethylpyrazine.

$[\alpha]_{26°}^D=-147°$ (c=1.1%), methyl alcohol.

EXAMPLE 23

(S,S)-2-(3-Chloropyrazin-2-yl)-5-methyl-2,5-diazabicyclo[2.2.1]heptane

The title compound is prepared by the procedure of Example 19 using 2,3-dichloropyrazine.

$[\alpha]_{26°}^D=-83°$ (c=0.29%), methylene chloride.

EXAMPLE 24

(S,S)-2-(6-Chloropyrazin-2-yl)-5-methyl-2.5-diazabicyclo[2.2.1] heptane

The title compound is prepared by the procedure of Example 19 using 2,6-dichloropyrazine.
mp= 125°–126° C.;

$[\alpha]_{26°}^D=-147°$ (c=1.2%), methyl alcohol.

EXAMPLE 25

(S,S)-2-Methyl-5-(1,2,4-thiadiazol-5-yl)-2,5-diazabicyclo[2.2.1]heptane

The title compound is prepared by the procedure of Example 19 using 5-chloro-1,2,4-thiadiazole.
MS(FAB): m/z 196 M$^+$.

EXAMPLE 26

(S,S)-2-Methyl-5-(3-methyl-1,2,4-thiadiazol-5-yl)-2,5-diazabicyclo[2.2.1] heptane The title compound is prepared by the procedure of Example 19 using 2-chloro-3-methyl-1,2,4-thiadiazole.
MS (FAB): m/z 210 M$^+$.

EXAMPLE 27

(S,S)-2-Methyl-5-(2-thiazolyl)-2,5-diazabicyclo[2.2.1] heptane

The title compound is prepared by the procedure of Example 19 using 2-chlorothiazole.

$[\alpha]_{26°}^D=-123°$ (c=1.0%), methyl alcohol.

EXAMPLE 28

(S,S)-2-Methyl-5-(3-nitro-2-thienyl)-2,5-diazabicyclo [2.2.1] heptane

A solution of 1.0 g of (S,S)-2-methyl-2,5-diazabicyclo [2.2.1] heptane, 1.5 g of 2-bromo-3-nitrothiophine, 1.5 g of diazabicyclo[ 3.6.0] unodecene in 30 ml of methylene chloride is stirred at room temperature for 16 hours. The mixture is diluted with methylene chloride and washed with 5N aqueous sodium hydroxide. The methylene chloride layer is dried and concentrated in vacuo. The residue is purified by plug filtration (aluminum oxide, activity grade 2.5; methylene chloride) to give the product as yellow crystals:

$[\alpha]_{26°}^D=+386°$ (c=0.8%), methyl alcohol.

EXAMPLE 29

(S,S)-2-Methyl-5-(5-nitro-2-thienyl)-2,5-diazabicyclo [2.2.1] heptane

The title compound is prepared by the procedure of Example 28 using 5-nitro-2-chlorothiophene.

$[\alpha]_{26°}^D=-392°$ (c=1.1%), methyl alcohol.

EXAMPLE 30

(S,S)-2-Methyl-5-(2-nitrophenyl)-2,5-diazabicyclo [2.2.1] heptane

The title compound is prepared by the procedure of Example 28 using 1-fluoro-2-nitrobenzene.

$[\alpha]_{26°}^D=+2,104$, (c=0.9%), methyl alcohol.

EXAMPLE 31

(S,S)-2-Methyl-5-(4-nitrophenyl)-2,5-diazabicyclo [2.2.1] heptane

The title compound is prepared by the procedure of Example using 1-fluoro-4-nitrobenzene.

$[\alpha]_{26°}^{D} = -416°$ (c=1.0%), methyl alcohol.

EXAMPLE 32

(S,S)-2-Methyl-5-(6-methoxypyrazin-2-yl)-2,5-diazabicyclo[2.2.1]heptane

A solution of 1.0 g of product from Example 24 in 10 ml of methyl alcohol and 3.8 ml of 3.5M sodium methoxide is heated at the reflux temperature overnight. The reaction is cooled, concentrated in vacuo and partitioned between water and methylene chloride. The organic layer is dried, concentrated in vacuo and the residue is purified by chromatography (aluminum oxide, Activity Grade 2.5; methyl alcohol/methylene chloride) to give 0.5 g of the desired product as an oil:

$[\alpha]_{26°}^{D} = -159°$ (c=1.0%), methyl alcohol.

EXAMPLE 33

(S,S)-2-(3-Methoxypyrazinyl)-5-methyl-2,5-diazabicyclo [2.2.1] heptane

The title compound is prepared by the procedure of Example 32 using the product from Example 23 and sodium methoxide.

$[\alpha]_{26°}^{D} = -93°$ (c=0.14%), methyl alcohol.

EXAMPLE 34

(S,S)-2-Methyl-5-(3-methyl-1,2,4-oxadiazol-5-yl)-2,5-diazabicyclo[2.2.1]heptane

The title compound is prepared by the procedure of Example 9 using (S,S)-2-methyl-2,5-diazabicyclo[2.2.1] heptane.

$[\alpha]_{26°}^{D} = -97°$ (c=2.1%), methyl alcohol.

EXAMPLE 35

(S,S)-2-Methyl-5-(3-methylpyrizin-2-yl)-2,5-diazabicyclo[2.2.1] heptane

The title compound is prepared by the procedure of Example 19 using 2-chloro-3-methylpyrazine.
MS (FAB): m/z 205 (M+H).

EXAMPLE 36

(R,R)-2-Methyl-5-(2-pyrazinyl)-2,5-diazabicyclo [2.2.1]heptane

The title compound is prepared by the procedure of Example 19 using (R,R,)-2-methyl-2,5-diazabicyclo[ 2.2.1] -heptane prepared by the procedure of U. Jordis et al, *Synthesis*, 1990, 925.

$[\alpha]_{26°}^{D} = +200°$ (c=0.2%), methyl alcohol.

We claim:

1. A compound of formula I or II;

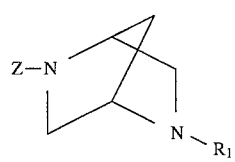

-continued

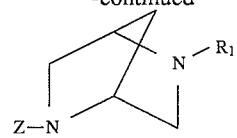

wherein
Z is hydrogen, methyl, $(C_1-C_{10})$alkyloxycarbonyl or benzyloxycarbonyl;
$R_1$ is

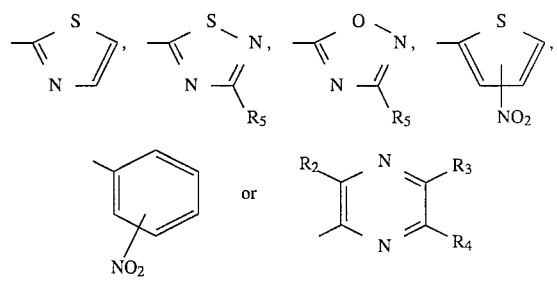

wherein $R_2$, $R_3$ and $R_4$ are hydrogen; halogen selected from bromine, chlorine, fluorine and iodine; $(C_1-C_6)$alkyl or $(C_1-C_6)$alkyloxy; and $R_5$ is hydrogen or $(C_1-C_6)$alkyl; or a pharmacologically acceptable salt thereof.

2. A compound of formula I or II:

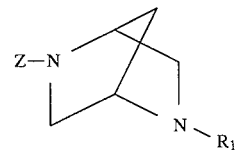

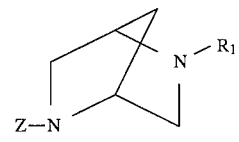

wherein
Z is hydrogen, methyl, $(C_1-C_{10})$alkyloxycarbonyl or benzyloxycarbonyl;
$R_1$ is

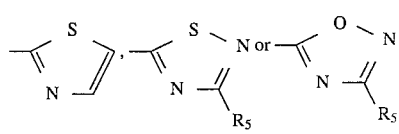

wherein
R5 is hydrogen or (C1–C6)alkyl; or a pharmacologically acceptable salt thereof.

3. A compound of formula I or II:

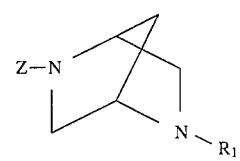

-continued

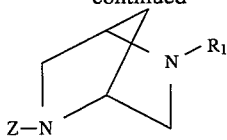

wherein
Z is hydrogen, methyl, (C₁–C₁₀) alkyloxycarbonyl or benzyloxycarbonyl;

R₁ is

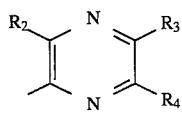

wherein R₂, R₃ and R₄ are hydrogen; halogen selected from bromine, chlorine, fluorine and iodine; (C₁–C₆) alkyl or (C₁–C₆) alkyloxy; or a pharmacologically acceptable salt thereof.

4. A compound of formula I or II:

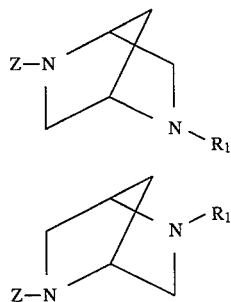

wherein
Z is hydrogen, methyl, (C₁–C₁₀)alkyloxycarbonyl or benzyl oxycarbonyl;

R1 is

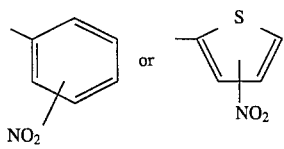

or a pharmacologically acceptable salt thereof.

5. A compound of formula I or II:

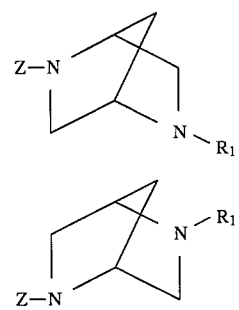

wherein
Z is hydrogen or (C₁–C₆)alkyl:

R1 is

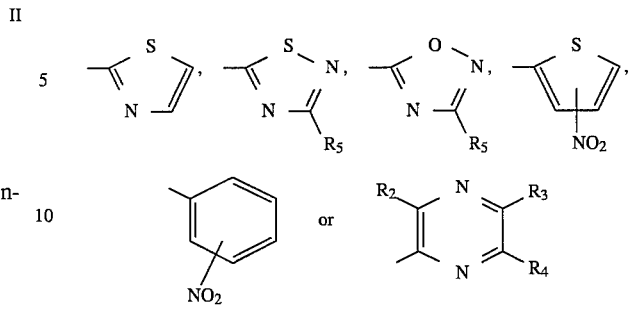

wherein R₂, R₃ and R₄ are hydrogen; halogen selected from bromine, chlorine, fluorine and iodine; (C₁–C₆)alkyl or (C₁–C₆)alkyloxy; and R₅ is hydrogen or (C₁–C₆)alkyl; or a pharmacologically acceptable salt thereof.

6. A compound of formula I or II:

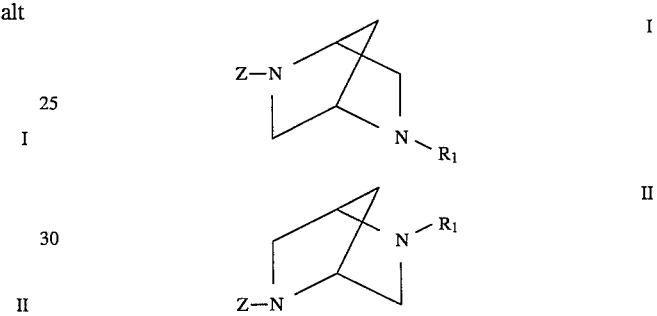

wherein
Z is (C₁–C₁₀) alkyloxylcarbonyl, arylmethyloxycarbonyl:

R1 is

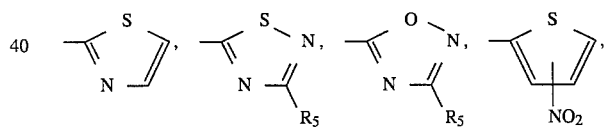

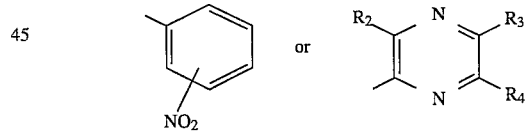

wherein R₂, R₃ and R₄ are hydrogen; halogen selected from bromine, chlorine, fluorine and iodine; (C₁–C₆)alkyl or (C₁–C₆)alkyloxy; and R₅ is hydrogen or (C₁–C₆)alkyl; or a pharmacologically acceptable salt thereof.

7. The compound according to claim 2, which is (R,R)-2-(tert-butyloxycarbonyl)-5-(3-methyl-1,2,4-oxadiazolyl)-2,5-diazabicyclo[ 2.2.1] heptane or a pharmaceutically acceptable salt thereof.

8. The compound according to claim 3, which is (S,S)-2-(tert-butyloxycarbonyl)-5-(3-methyl-1,2,4-oxadiazol-5-yl)-2,5-diazabicyclo[2.2.1]heptane or a pharmaceutically acceptable salt thereof.

9. The compound according to claim 2, which is (R,R)-2-(tert-butyloxycarbonyl)-5-(2-pyrazinyl)-2,5-diazabicyclobicyclo[ 2.2.1] heptane or a pharmaceutically acceptable salt thereof.

10. The compound according to claim 2, which is (R,R,)-2-(tert-butyloxycarbonyl-5-(1,2,4-thiadiazol-5-yl)- 2,5-diazabicyclo[2.2.1] heptane or a pharmaceutically acceptable salt thereof.

11. The compound according to claim 2, which is (S,S)-2-(tert-butyloxycarbonyl)-5-(1,2,4-thiadiazol-5-yl)- 2,5-diazabicyclo[2.2.1] heptane or a pharmaceutically acceptable salt thereof.

12. The compound according to claim 2, which is (R,R)-2-(tert-butyloxycarbonyl)-5- (3-methyl-1,2,4-thiadiazol- 5-yl)-2,5-diazabicyclo[2.2.1] heptane or a pharmaceutically acceptable salt thereof.

13. The compound according to claim 2, which is (S,S)-2-(tert-butyloxycarbonyl)-5-(3- methyl-1,2,4-thiadiazol- 5-yl)-2,5-diazabicyclo[2.2.1] heptane or a pharmaceutically acceptable salt thereof.

14. The compound according to claim 2, which is (R,R)-2-(3-methyl-1,2,4-oxadiazo-5-yl)-2,5-diazabicyclo[2.2.1] heptane or a pharmaceutically acceptable salt thereof.

15. The compound according to claim 2, which is (S,S)-2-(3- methyl-1,2,4-oxadiazol-5-yl)-2,5-diazabicyclo[2.2.1] heptane or a pharmaceutically acceptable salt thereof.

16. The compound according to claim 3, which is (R,R)-2-(2- pyrazinyl)-2,5-diazabicyclo[2.2.1] heptane or a pharmaceutically acceptable salt thereof.

17. The compound according to claim 3, which is (S,S)-2-(2-pyrazinyl)-2,5-diazabicyclo[2.2.1] heptane or a pharmaceutically acceptable salt thereof.

18. The compound according to claim 2, which is (R,R)-2-(1,2,4-thiadiazol-5-yl)-2,5-diazabicyclo[2.2.1] heptane.

19. The compound according to claim 2, which is (S,S)-2-(1,2,4-thiadiazol-5-yl)-2,5-diazabicyclo[2.2.1] heptane or a pharmaceutically acceptable salt thereof.

20. The compound according to claim 2, which is (R,R)-2-(3-methyl-1,2,4- thiadiazol-5-yl)-2,5-diazabicyclo[2.2.1] heptane or a pharmaceutically acceptable salt thereof.

21. The compound according to claim 2, which is (S,S)-2-(3-methyl-1,2,4- thiadiazol-5-yl)-2,5-diazabicyclo[2.2.1] heptane or a pharmaceutically acceptable salt thereof.

22. The compound according to claim 4, which is (S,S)-2-methyl-5-(3-nitro-2-thienyl)-2,5- diazabicyclo[2.2.1] heptane.

23. The compound according to claim 4, which is (S,S)-2-methyl-5-(2-nitrophenyl)-2,5-diazabicyclo[2.2.1] heptane or a pharmaceutically acceptable salt thereof.

24. The compound according to claim 3, which is (R,R)-2-methyl-5-(2-pyrazinyl)-2,5-diazabicyclo[2.2.1] heptane or a pharmaceutically acceptable salt thereof.

25. The compound according to claim 3, which is (S,S)-2-methyl-5-(2-pyrazinyl)-2,5-diazabicyclo[2.2.1] heptane or a pharmaceutically acceptable salt thereof.

26. The compound according to claim 3, which is (S,S)-2-(3,6-dimethylpyrazin-2-yl)-5-methyl-2,5-diazabicyclo [2.2.1] heptane or a pharmaceutically acceptable salt thereof.

27. The compound according to claim 3, which is (S,S)-2-(3-chloropyrazin-2-yl)-5-methyl-2,5-diazabicyclo[2.2.1] heptane or a pharmaceutically acceptable salt thereof.

28. The compound according to claim 3, which is (S,S)-2-(3-methoxypyrizin-2-yl)-5-methyl-2,5-diazabicyclo [2.2.1] heptane or a pharmaceutically acceptable salt thereof.

29. The compound according to claim 3, (S,S)-2-methyl-5-(3-methylpyrazin-2-yl)-2,5-diazabicyclo[2.2.1] heptane or a pharmaceutically acceptable salt thereof.

30. The compound according to claim 3, which is (S,S)-2-(6-chloropyrazin-2-yl)-5-methyl-2,5-diazabicyclo[2.2.1] heptane.

31. The compound according to claim 3, which is (S,S)-2-methyl-5-(3-methyl-1,2,4-oxadiazol-5-yl)-2,5-diazabicyclo[2.2.1] heptane.

32. The compound according to claim 2, which is (S,S)-2-methyl-5-(3-methyl-1,2,4-thiadiazol-5-yl)-2,5-diazabicyclo[2.2.1] heptane.

33. The compound according to claim 2, which is (S,S)-2-methyl-5-(2-thiazolyl)-2,5-diazabicyclo[2.2.1] heptane.

* * * * *